US008554303B2

(12) United States Patent
Atalar et al.

(10) Patent No.: US 8,554,303 B2
(45) Date of Patent: Oct. 8, 2013

(54) MAGNETIC RESONANCE RF COIL ASSEMBLY FOR IMAGING OF THE CERVICAL REGION

(76) Inventors: Ergin Atalar, Ankara (TR); Nikolay V. Visksenko, Ankara (TR)

( * ) Notice: Subject to any disclaimer, the term of this patent is extended or adjusted under 35 U.S.C. 154(b) by 251 days.

(21) Appl. No.: 13/086,577

(22) Filed: Apr. 14, 2011

(65) Prior Publication Data
US 2011/0257515 A1 Oct. 20, 2011

Related U.S. Application Data

(60) Provisional application No. 61/325,210, filed on Apr. 16, 2010.

(51) Int. Cl.
*A61B 5/055* (2006.01)
(52) U.S. Cl.
USPC ............................ 600/414; 411/422; 411/423
(58) Field of Classification Search
USPC .................. 600/410, 411, 414, 417, 421–423
See application file for complete search history.

(56) References Cited

U.S. PATENT DOCUMENTS

| 6,549,800 | B1 * | 4/2003 | Atalar et al. ................. 600/423 |
| 2005/0215886 | A1 * | 9/2005 | Schmidt ....................... 600/423 |
| 2010/0168555 | A1 * | 7/2010 | Karmarkar et al. ........... 600/423 |

OTHER PUBLICATIONS

"Intravascular Magnetic Resonance Imaging Using a Loopless Catheter Antenna," Ocali et al., Magnetic Resonance in Medicine, vol. 37 (1997) pp. 112-118.

* cited by examiner

Primary Examiner — Ruth S Smith
(74) Attorney, Agent, or Firm — Schiff Hardin LLP

(57) ABSTRACT

A radio-frequency (RF) coil for obtaining magnetic resonance data for imaging the cervical region of a patient has a loop coil contained in a housing of an applicator assembly that is adapted for placement against the cervix of the patient, and a loopless antenna contained in a tandem applicator of the assembly, that is adapted for intracorporeal placement in the cervix of the patient.

6 Claims, 6 Drawing Sheets

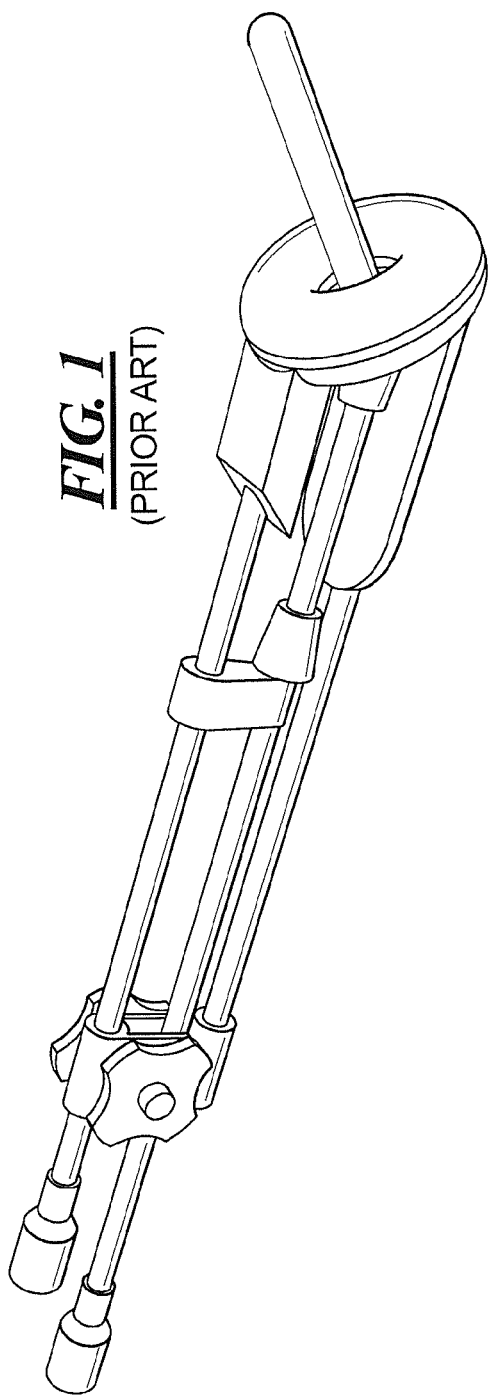
FIG. 1
(PRIOR ART)
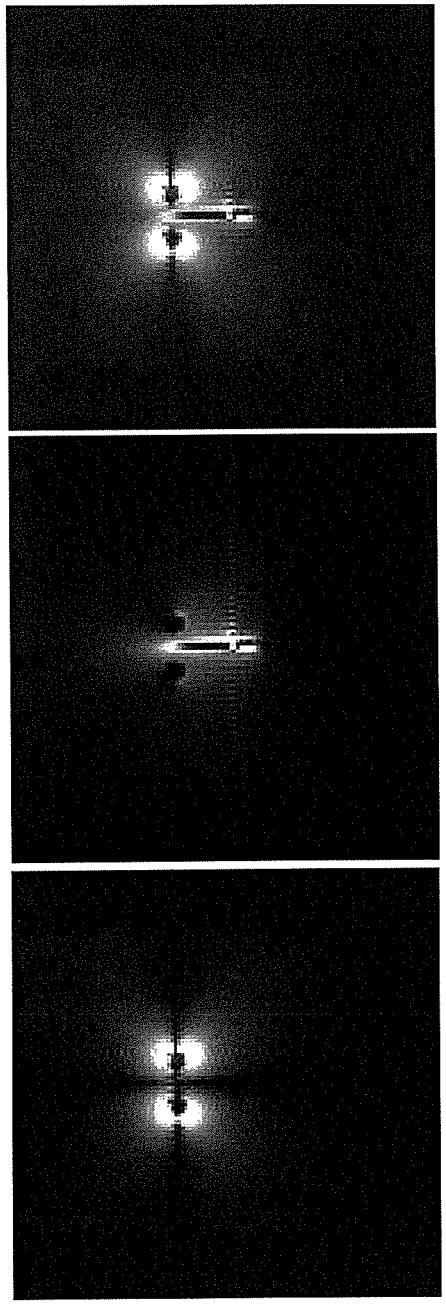
FIG. 2A
FIG. 2B
FIG. 2C

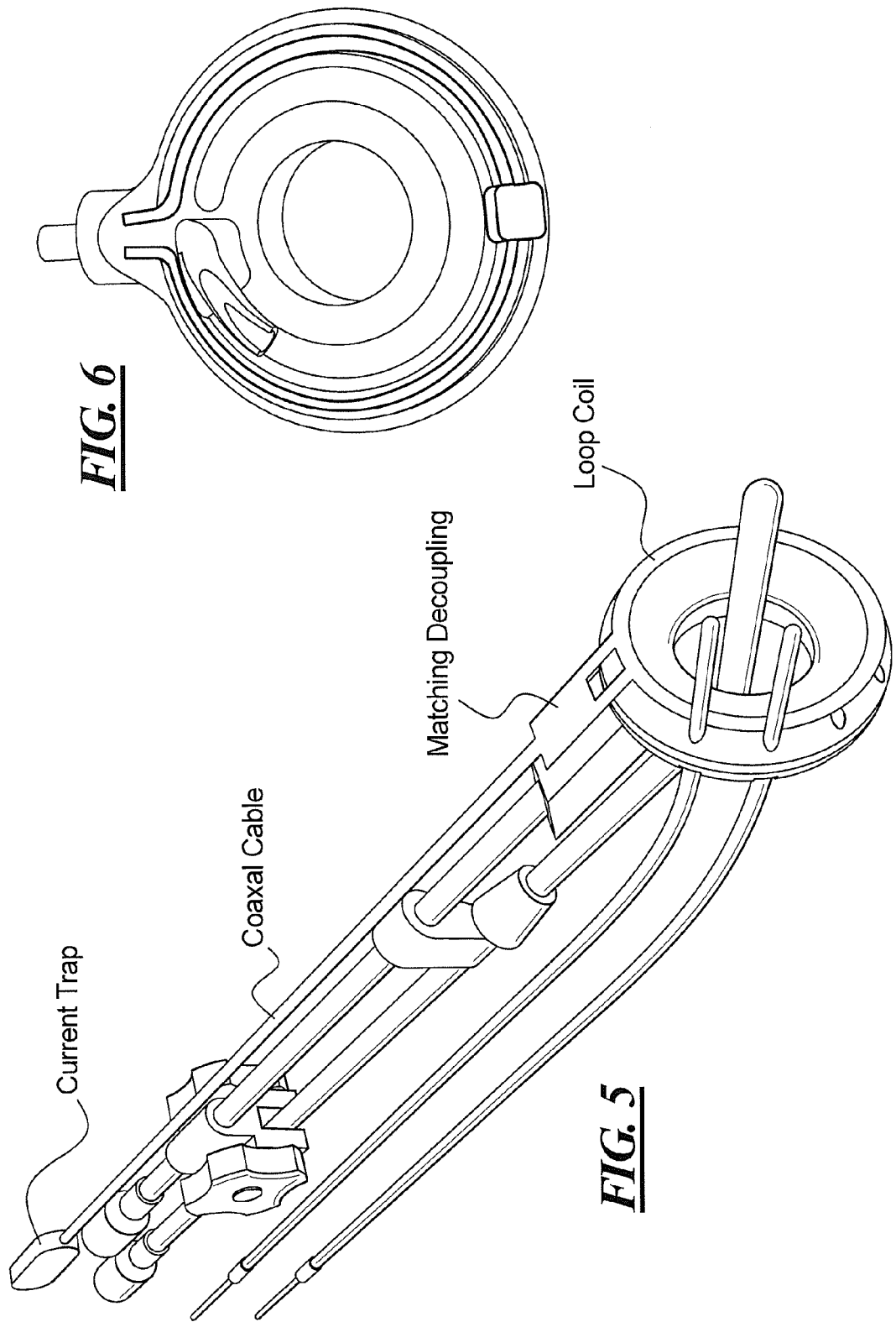

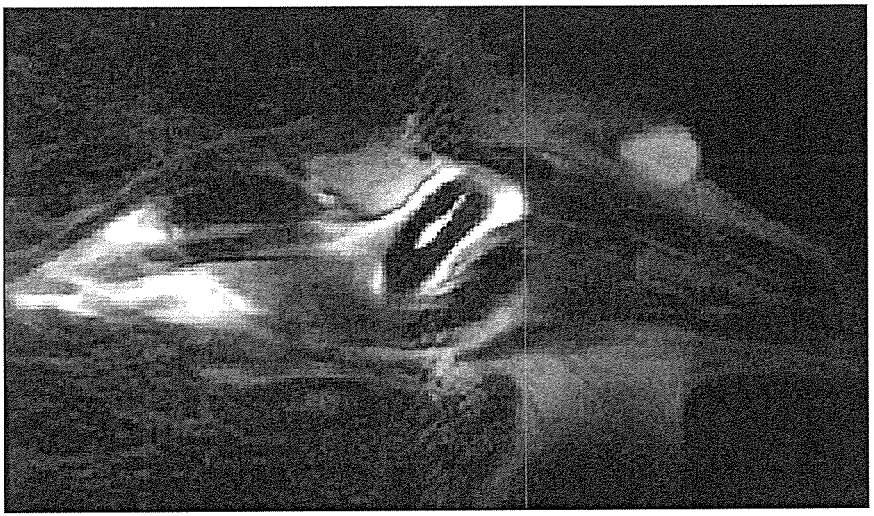
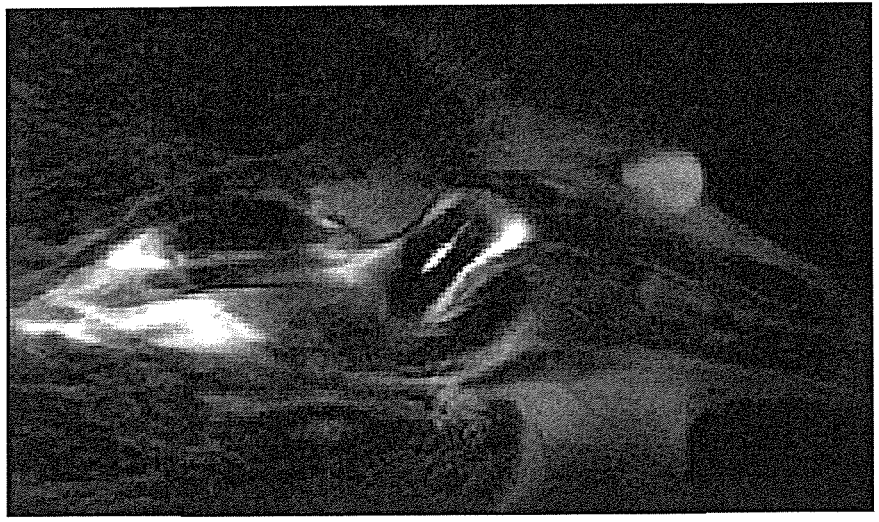

MAGNETIC RESONANCE RF COIL ASSEMBLY FOR IMAGING OF THE CERVICAL REGION

RELATED APPLICATION

The present application claims the benefit of the filing date of Provisional Application 61/325,210, filed Apr. 16, 2010.

BACKGROUND OF THE INVENTION

1. Field of the Invention

The present invention concerns a magnetic resonance radio-frequency (RF) coil assembly that is designed for obtaining magnetic resonance data for imaging the cervical region.

2. Description of the Prior Art

A ring applicator for cervical brachytherapy procedures monitored by computed tomography or magnetic resonance imaging is commercially available from Nucletron (Utrecht, Netherlands). This applicator is shown in FIG. 1 and is formed by a loop and a tandem applicator. The loop applicator is configured to be located extracorporeally adjacent to the cervix, and the tandem applicator proceeds through the interior of the loop, and is placed into the cervix in a pre-treatment procedure. The tandem applicator is aligned so as to be perpendicular to the planar surface defined by the loop.

The brachytherapy procedure that is implemented using this known applicator can be monitored, as noted above, by computed tomography or by magnetic resonance imaging. In the case of monitoring by magnetic resonance imaging, conventionally designed, general purpose local coils, or if appropriate a whole-body coil, are used for RF transmission and/or reception, in order to generate and acquire the magnetic resonance data in an appropriate imaging sequence. Because these RF coils are among the conventional coils that are available for a number of different imaging purposes, they do not have a specific design for cervical imaging, and must be placed on or around the body of the patient at manually selected locations, according to the judgment and experience of the technician or physician responsible for implementing the procedure. Because these conventional coils do not conform to the anatomy of the cervical region, the signal-to-noise ratio (SNR) of the transmitted and/or received signals may suffer due to compromises that must be made in the placement of such coils relative to the cervix. A sub-optimum SNR results in an image of sub-optimum clarity for diagnostic purposes.

SUMMARY OF THE INVENTION

In accordance with the present invention, the aforementioned, known brachytherapy applicator is modified to include an RF loop coil and an RF loopless antenna that transmit and receive RF signals in a magnetic resonance imaging sequence. Since the known applicator is already adapted for optimum placement with respect to the cervical region of a patient, the loop coil and the loopless antenna allow magnetic resonance signals to be detected with significantly improved SNR, compared to conventional local coils.

In accordance with the invention, the loop antenna is embedded in the applicator loop, and the loopless antenna is embedded or embodied in the tandem applicator. Although the loop coil is highly sensitive to the region surrounding it, the loop coil has a null sensitivity at its center, with the access of the loop coil being approximately along the main magnetic field direction. By contrast, the loopless antenna is very sensitive to the region surrounding it, and therefore the combination of a loopless antenna located at the center of a loop antenna compensates for the nullity of the loop antenna inside the cervix. The position and shape of the tandem applicator in the known brachytherapy applicator are ideal for the placement of a loopless antenna inside the tandem applicator. The loopless antenna can be inserted into the tandem applicator temporarily during the acquisition of magnetic resonance data, and can be removed during brachytherapy, so as to be replaced by the radioactive source. As a result, high quality image of the cervix and the surrounding tissue are achieved by the signals transmitted and detected by a combination of the two coils.

BRIEF DESCRIPTION OF THE DRAWINGS

FIG. 1, as noted above, is a perspective view of a known, commercially available cervical applicator for a brachytherapy procedure.

FIG. 2A shows the sensitivity of a loop coil by itself, FIG. 2B shows the sensitivity of a loopless coil or antenna by itself, and FIG. 2C shows the sensitivity of a combination of a loop coil and a loopless antenna.

FIG. 5 shows a cervical applicator for a magnetic resonance imaging in accordance with the present invention.

FIG. 6 shows the interior of the loop applicator with recesses for receiving the components associated with the loop coil.

FIG. 8A is a T2-weighted magnetic resonance coronal image of a female canine obtained with the loopless coil in accordance with the present invention, FIG. 8B shows a T2-weighted magnetic resonance coronal image of the female canine obtained with a loop coil in accordance with the present invention, and FIG. 8C is a combination of the images in FIGS. 8A and 8B.

DESCRIPTION OF THE PREFERRED EMBODIMENTS

Loopless Antenna

Figure 3:
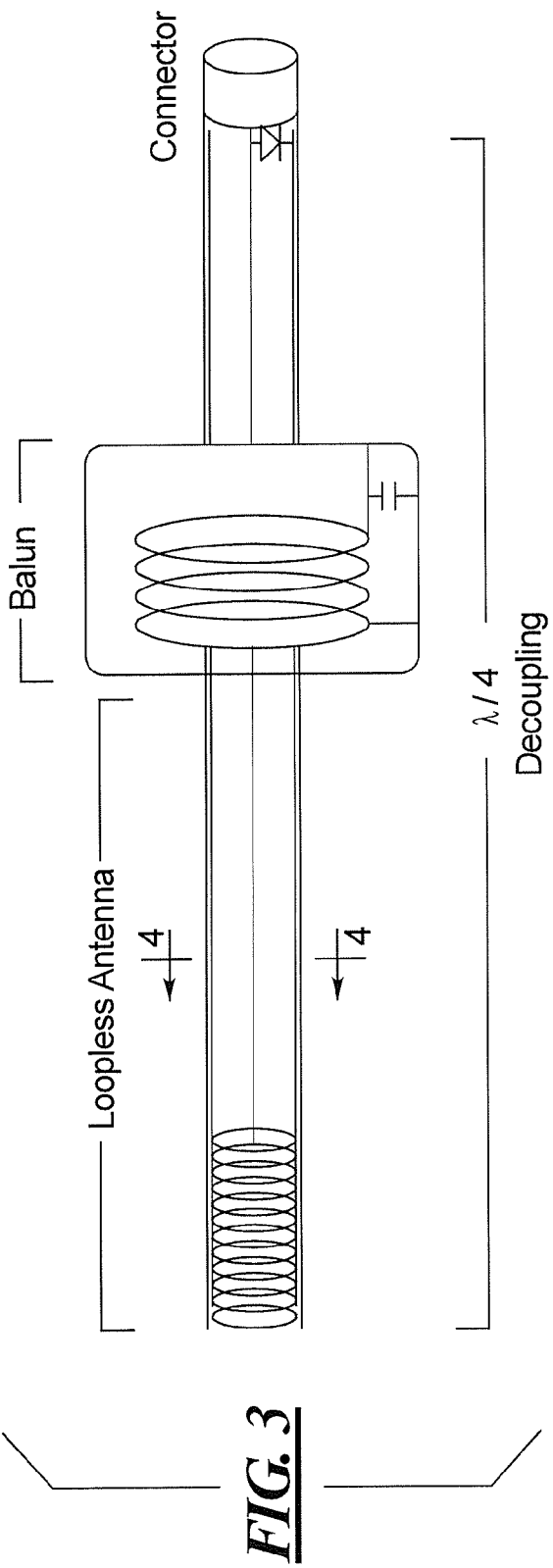
FIG. 3 schematically illustrates the structure of a loopless antenna in accordance with the present invention.

The design of the Loopless coil is shown in FIG. 3. The probe is housed inside a tandem applicator. The probe includes a loopless antenna, decoupling/matching circuits and a balun. In the following subsections, the components of the probe are described.

FIG. 2A is an image obtained with a phantom illustrating the sensitivity of a loop coil in accordance with the present invention by itself. FIG. 2B shows the sensitivity of a loopless coil or antenna in accordance with the present invention by itself. FIG. 2C shows the combined sensitivity of a loop coil and a loopless coil in accordance with the present invention.

The loopless antenna is a coaxial cable with extended inner conductor and is used for receiving signal during a magnetic resonance imaging examination. Since it has a very small profile, it can be used in the body cavities for the purpose of acquiring high signal-to-noise ratio images around the region it is placed. In this work, the loopless antenna is used inside a brachytherapy tandem applicator that can be placed inside the cervix with the aim of high-resolution imaging of cervix.

Figure 4:
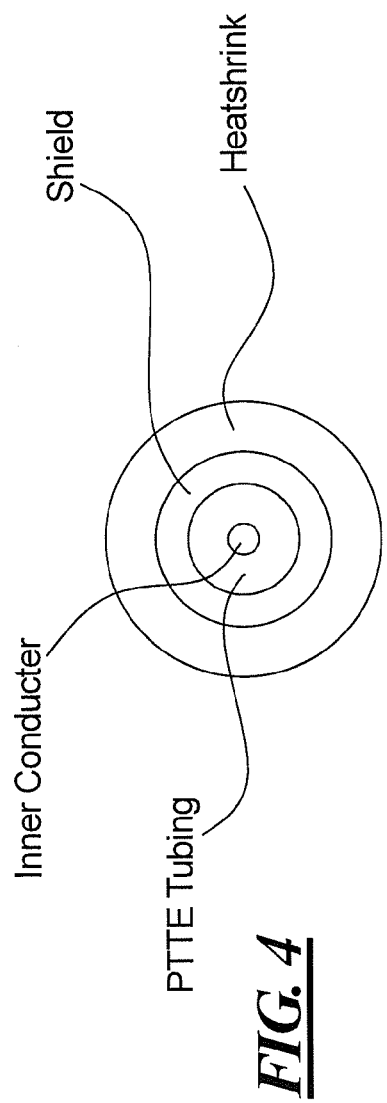
FIG. 4 is a sectional view taken along line IV-IV in FIG. 3.

Details of the design are shown in section in FIG. 4. The coaxial portion of the design is constructed by using PTFE tubing with inner diameter of 1 mm, outer diameter of 1.3 mm. The length of the wire is adjusted to quarter wavelength. The tubing is covered with a copper braid with a wall thickness of 0.25 mm. A 32AWG magnet wire is used as inner conductor. The extended inner conductor is coiled with diameter of 2.13 mm and length of 3.6 cm. The number of the winding of the coil is 186. A BNC connector is soldered to the proximal end of the loopless antenna. All structure is covered with a polyester heatshrink with wall thickness of 0.076 mm.
Balun Balun (Balanced-Unbalanced Transformer) is a frequently used circuit in many applications including microwave circuits and antenna. In this application, it is used to prevent shield currents on the coaxial cables. The unwanted shield currents may affect the signal uniformity and also may cause excessive heating.

The design of the balun used in this application is shown in FIG. 3. The balun is placed in the middle of the coaxial cable and is 33 cm away from the distal end and 48 cm away from the proximal end. The balun is constructed by winding the coaxial cable in 4 loops and placing it inside a cylindrical copper box with 2.5 cm diameter and 3.5 cm length. At the proximal end of the balun the outer conductor of the probe is shorted to the copper box and then the balun was tuned using a single ATC magnetic resonance compatible B type 70 pF capacitor.
Matching and Decoupling The aim of the decoupling circuit is to prevent induced currents on the probe during RF transmission by the body coil. Decoupling is achieved by simply placing a shunt PIN diode at the proximal end of coaxial cable as shown in FIG. 3. When the diode is on, the quarter wavelength wire transforms the low impedance of the diode to a high impedance value at the distal end of the coaxial cable and hence decreases induced currents.

In this design, no tuning is required for matching because the loopless antenna's impedance is already very close to the characteristic impedance of the coaxial cable.
Testing Testing of the endocervical MR probe can be separated into three main parts: electrical testing, safety testing, and imaging.
Electrical Testing Antenna impedance: Antenna impedance is an important parameter for the performance of the loopless antenna. In an article by Ocali et al. "Intravascular Magnetic Resonance Imaging Using a Loopless Catheter Antenna," Magnetic Resonance in Medicine, Vol. 37 (1), p. 112-118 (1997), it was shown that the square root of the real component of the antenna impedance is inversely proportional with signal-to-noise ratio. In the bare-wire antenna case, the minimum observed impedance was 35 ohms. It was shown that when the antenna is insulated because of some practical requirements, the real part of the impedance goes up and degrades the SNR performance of the design.

In order to understand the performance of the design, we have measured antenna impedance inside the brachytherapy applicator. Salinated water (4% salt) was used to mimic human cervix. The length of the coiled portion of the loopless antenna was optimized in order to minimize the antenna impedance. 62 ohms was obtained when the coil length was 3.6 cm.

Although this impedance higher than 35 ohms that was obtained by the bare-wire antennas, loss of 33% reduction in SNR reduction (square root of 62/35) is acceptable for this application.

Characteristic impedance: When the characteristic impedance of the coaxial cable matches the antenna impedance, the signal transmission is obtained with minimum loss. In most coils there is a significant difference between coaxial cable impedance and the antenna impedance and therefore a matching circuit is needed. In loopless design as mention above the antenna impedance was found to be 62 ohms. If the characteristic impedance of the coaxial cable that we built matches this value, there will be no need for the matching circuit.

In order to measure the characteristic impedance of the manufactured coaxial cable, a 50 ohm load is connected to quarter wavelength coaxial cable and impedance is measured as 59 ohms. Therefore the characteristic impedance is calculated (square root of 50×59) as 54 ohms. This is in an acceptable range of 62 ohms and therefore there is no need for matching circuit.

Balun: Balun circuit increases the series impedance of the shield of the coaxial cable without affecting its transmission properties. The impedance of the balun was measured by a network analyzer as 3 kohm at 123.23 MHz. The adequacy of this value is later tested by heating and imaging tests.

Decoupling: The performance of the decoupling circuit is measured as the impedance of the antenna during RF transmission. Siemens 3T Trio scanners provide a DC bias current during this period. The PIN diode in the circuit turns on and its RF impedance becomes low. Quarter wavelength coaxial cable transforms this low impedance value to a high impedance value. Depending on the loss on the coaxial cable this value of this high impedance may vary. However, the effectiveness of the decoupling circuit high depends on this impedance value.

Figure 7:
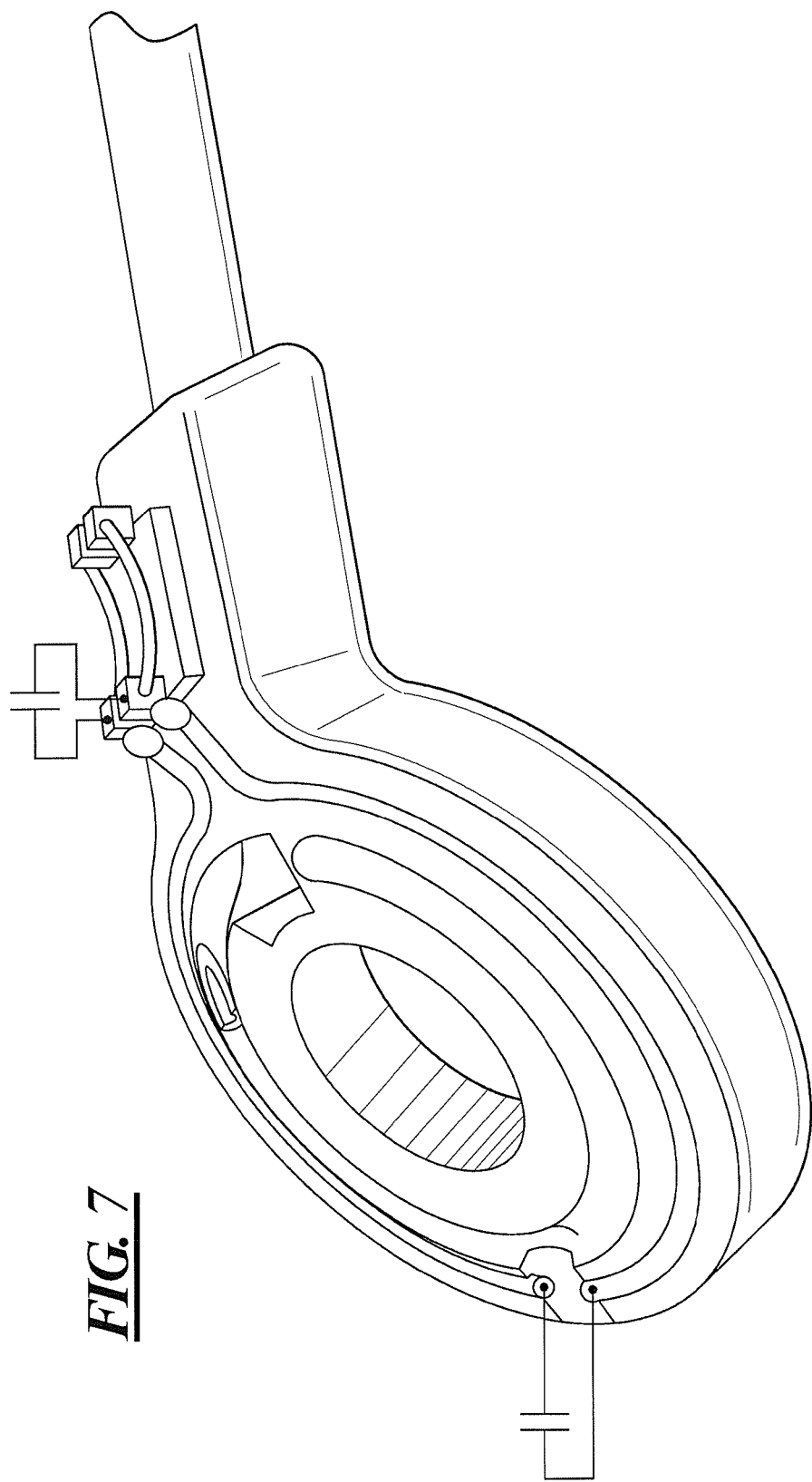
FIG. 7 shows the interior of the loop applicator with the components associated with the loop coil mounted therein.

For the purpose of understanding the performance of the decoupling circuit we have measured impedance of the shorted quarter wavelength coaxial cable as 2.8 k ohm. This value is significantly higher than the antenna impedance of 62 ohms suggesting significant suppression of induced currents. Further testing of the decoupling performance was done using imaging experiments.
Loop Coil for Endocervical Magnetic Resonance Imaging The basic design of the loop coil is shown in FIGS. 6 and 7. The coil has a loop coil, decoupling/matching circuits, coaxial cable and balun (current trap). In the following subsections, the components of the probe are described in detail.
Manufacturing Process The loop coil was embedded into the Nucletron CT-MR ring applicator which has 60° angle and 3.7 cm diameter. The ring applicator was cut into two parts with the help of the CNC and then a new 3.3 cm groove was opened for the loop coil (FIG. 6).
Loop Coil The loop coil was created by a capper magnet wire with 1 mm diameter. The wire was shaped such that it could be embedded into the previously opened groove (FIG. 7).
Tuning and Matching The coil was tuned with two parallel 20 and 3.9 pF ATC nonmagnetic capacitor matched with a single 270 pF capacitor (FIG. 7). The measured impedance of the loaded coil was 52 ohm at 123.23 Mhz.

Decoupling

The aim of the decoupling circuit is to prevent induced currents on the probe during RF transmission by the body coil. Decoupling is achieved by placing a shunt PIN diode at the proximal end of micro strip. The micro strip is formed by two parallel conductors affixed to an insulating carrier. The conductors may be approximately 2 mm wide and spaced from each other by approximately 3 mm. When the diode is on, the circuit transforms the low impedance of the diode to a high impedance value at the loop coil and hence decreases induced currents.

In order to create the decoupling circuit the matching capacitor was removed from the coil and soldered to the distal end of the micro strip. Then the proximal end of the micro strip was shorted and the impedance on the capacitor was measured. The distance of the short circuit to the capacitor is adjusted such that the measured impedance would be real.

A 240 ohm real impedance was observed when the distance between capacitor and short circuit was adjusted to 12 mm. Then the short circuit is replaced with a Macom Ma4p1461f-1072 PIN diode and the decoupling circuit is soldered to the loop coil (FIG. 15).

The size of the decoupling circuit can be minimized and embedded into the applicator.

Connection to the Scanner

The loop coil is connected to the MR scanner using a 40 cm 50 ohm RG58 coaxial cable with a nonmagnetic connector at the distal end.

Two Channel Cervix Coil

An illustration of a complete version of the modified ring applicator is given in FIG. 5. The diameter of the loop antenna is adjusted such that it could be easily inserted into the applicator during the imaging and taken out during the radiation brachytherapy procedure.

Both channels of the coils were connected for the aforementioned testing to the MR scanner with nonmagnetic SMA connector. However, in order to satisfy clinical requirements, a medical connector that will be sterilizable and therefore reusable will be used instead.

Testing

Testing of the coil can be separated into two main parts: phantom imaging experiments and animal experiments.

Phantom Imaging Experiment

Imaging experiments are crucial in order to test the coil performance. With this motivation, we designed a cylindrical (water with 4 gr/lt copper sulfate and 1 gr/lt salt) phantom with 22 cm diameter and 35 cm length. Kiwi was used in order to simulate human cervix.

The phantom is placed in the center of the Siemens Trio 3T MR scanner and the endocervical magnetic resonance coil is placed at the center of the phantom. Imaging parameters are T1-weighted Turbo Spin Echo, TR/TE=800/12, slice thickness 2.6 mm, FOV read 150 mm, FOV phase 100 mm, Averages 2 Concatenation 2, Distance Factor 30%, number of slices 15, BW=260 Hz/pixel.

In order to evaluate the performance of the coil, a kiwi phantom was also imaged with the body matrix coil using same parameters.

The SNR of the image obtained using the endocervix coil is measured as approximately 5 times higher than the SNR of the image obtained using a body matrix coil.

Animal Experiments

An in-vivo canine experiment was made using a Siemens 3T Trio scanner. A turbo spin echo sequence was used with the following imaging parameters: a slice thickness=4 mm, TR=6 seconds, TE=114 milliseconds, pixel bandwidth 250 Hz/pixel, flip angle=120 degrees, the field-of-view=20 by 20 centimeters. The resulting T2-weighted coronal images of the female canine are given in FIG. 8. FIGS. 8A, 8B and 8C was obtained solely with the loopless coil. All of the pelvic space is highly visible. In FIG. 8B, the image obtained with the loop coil is given. The region between the cervical canal and the uterine cavity can be seen easily. In the loop coil image (FIG. 8B), endometrium and internal os can be observed much better than the conventional MR imaging strategies (FIG. 8A). In FIG. 8C, the combined image is shown. The cervix, uterus and all pelvic viscera can be clearly seen in the combined image.

Further Embodiments

Figure 9:
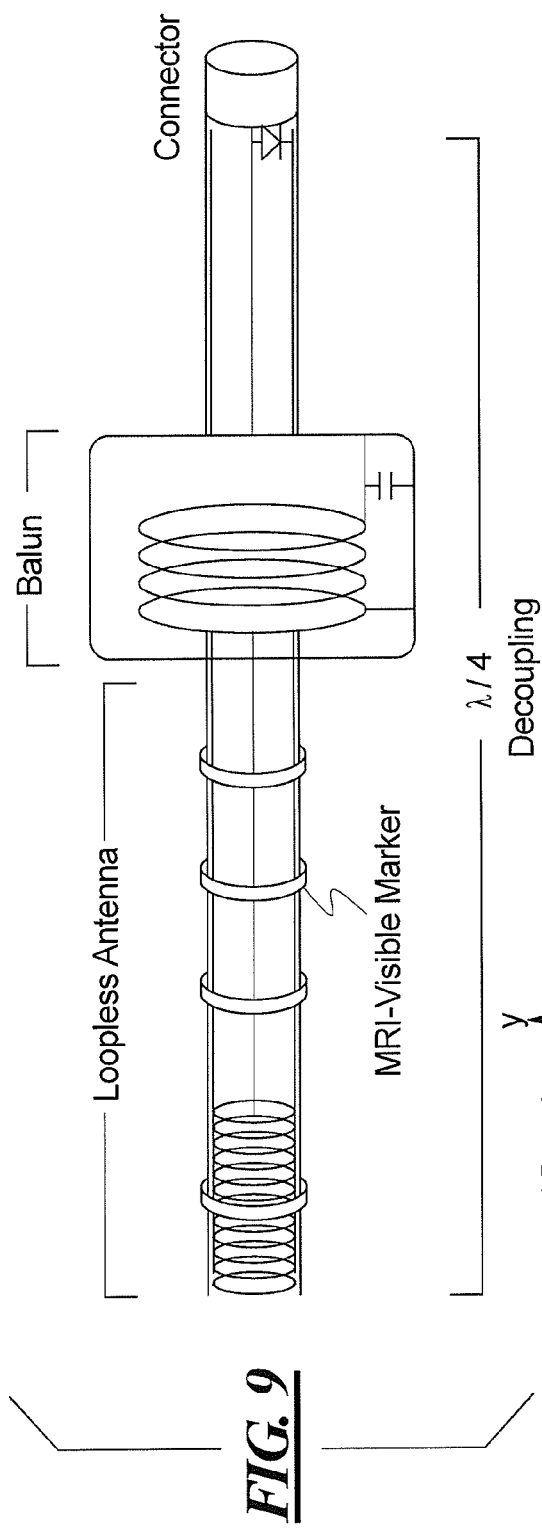
FIG. 9 schematically illustrates a further embodiment of the tandem applicator in accordance with the invention, which includes a number MRI-visible markers.

As shown in FIG. 9, the tandem applicator can be provided with one or more MRI-visible markers, such as metal rings that proceed around the exterior of the applicator housing. These markers are visible in a magnetic resonance image obtained with the coil assembly in place at a patient in an MRI apparatus. The markers allow the position and orientation of the applicator to be identified from the magnetic resonance image.

Figure 10:
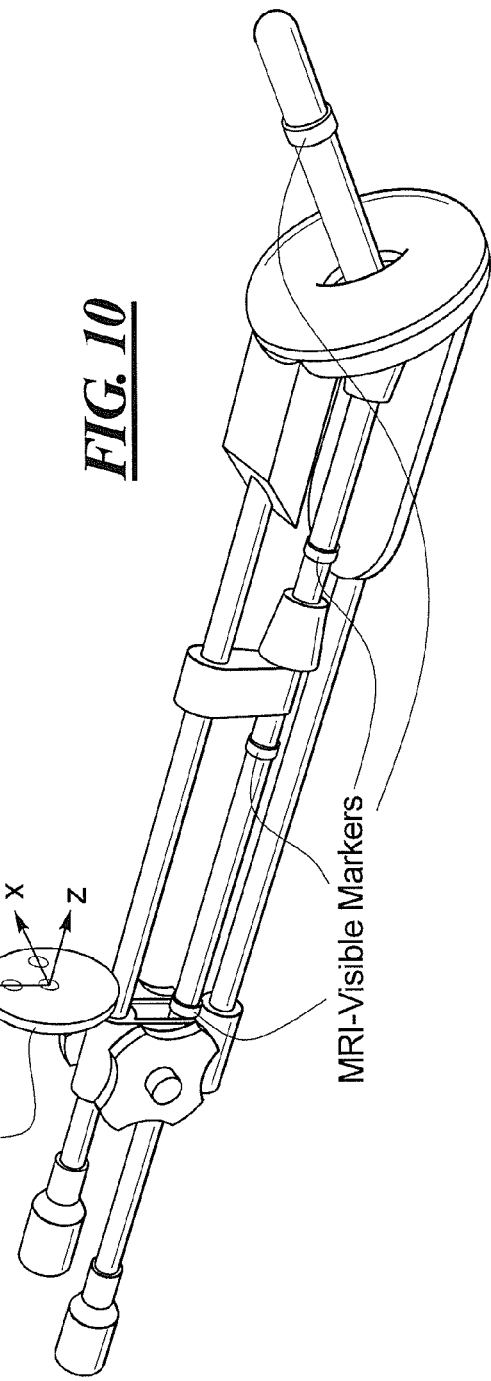
FIG. 10 is a perspective view of the assembly according to the invention, which MRI-visible markers on the tandem applicator, and a control panel with MRI-visible indicators also mounted to the assembly.

A further embodiment employing MRI-visible markers is shown in FIG. 10 wherein, in addition to MRI-visible markers located on the tandem applicator housing, or the conductor therefor, a control panel is attached to the assembly. The control panel has three indicators thereon that are visible in a magnetic resonance image, which designate the axes of a Cartesian coordinate system, in order to further assist determination of the position and orientation of the overall assembly in a magnetic resonance image of a patient with the applicator applied thereto.

Conclusion

The invention a simple two-channel coil designed that can easily be mounted on a ring HDRB applicator. The coils produce high signal intensity in the target region and the cervix, the uterus and all the pelvic viscera can be clearly seen from the obtained in-vivo images. It should be noted that these coils are designed for human anatomy, hence their structure is not very suitable for animal anatomy. As a result, the performances of the coils drop, but the inventive structure introduces improvements over the current techniques.

Although modifications and changes may be suggested by those skilled in the art, it is the intention of the inventors to embody within the patent warranted hereon all changes and modifications as reasonably and properly come within the scope of their contribution to the art.

We claim as our invention:

1. A radio-frequency (RF) coil assembly for transmitting and receiving RF signals in a magnetic resonance imaging sequence for obtaining an image of the cervical region of a patient, said assembly comprising:

an applicator assembly comprising a circular housing having a housing shape configured for extracorporeal placement against the cervical region of a patient, and a tandem applicator housing proceeding through a center of the circular housing and configured for intracorporeal placement in the cervix of the patient;

a loop coil contained in said circular housing and having a coil diameter conforming to said housing shape, said loop coil forming a loop antenna;

a loopless antenna contained in said tandem applicator housing, said loopless antenna having a loopless antenna axis proceeding therethrough;

said loop coil being disposed in a plane in said circular housing that is substantially orthogonal to said loopless antenna axis;

a first electrical conductor connected at a first end to said loop coil, and having a second end comprising a connector adapted for supplying RF energy to said loop coil and for emitting RF signals detected by said loop coil functioning as said loop antenna; and a second electrical conductor connected at a first end to said loopless antenna, and having a second end comprising a connector adapted for supplying RF energy to said loopless antenna and for emitting RF signals detected by said loopless antenna.

2. A coil assembly as claimed in claim 1 wherein said second electrical conductor comprises a balun connected between said loopless antenna and said connector.

3. A coil assembly as claimed in claim 1 wherein said loop coil comprises a tuning capacitor connected therein.

4. A coil assembly as claimed in claim 1 wherein said loop antenna comprises a decoupling circuit connected between said loop antenna and said first conductor.

5. A coil assembly as claimed in claim 1 comprising a plurality of MRI-visible markers located along said tandem applicator housing.

6. A coil assembly as claimed in claim 5 comprising an indicator carrier attached to said applicator assembly, said indicator carrier having a planar carrier surface with three MRI-visible indicators thereon that respectively indicate three axes of a Cartesian coordinate system.

* * * * *